United States Patent [19]

Fijiwara et al.

[11] Patent Number: 4,804,749
[45] Date of Patent: Feb. 14, 1989

[54] 20-O-ACYL-19,20-ENOLMACROLIDE ANTIBIOTIC DERIVATIVES

[75] Inventors: Tatsuro Fijiwara; Hideyuki Watanabe, both of Shizuoka; Hideo Sakakibara, Mishima, all of Japan

[73] Assignee: Toyo Jozo Co., Ltd., Shizuoka, Japan

[21] Appl. No.: 36,456

[22] Filed: Apr. 9, 1987

[30] Foreign Application Priority Data

Apr. 15, 1986 [JP] Japan ................... 61-86791

[51] Int. Cl.$^4$ .......................... C07H 17/08
[52] U.S. Cl. ............................. 536/7.1
[58] Field of Search ......................... 536/7.1

[56] References Cited

U.S. PATENT DOCUMENTS 4,252,898 2/1981 Nash et al. .................. 536/7.1
4,656,258 4/1987 Turner et al. ............... 536/7.1

Primary Examiner—Johnnie R. Brown
Assistant Examiner—Elli Peselev
Attorney, Agent, or Firm—Oblon, Fisher, Spivak, McClelland & Maier

[57] ABSTRACT

20-O-Acyl-19,20-enolmacrolide antibiotic derivatives represented by the following general formula (I):

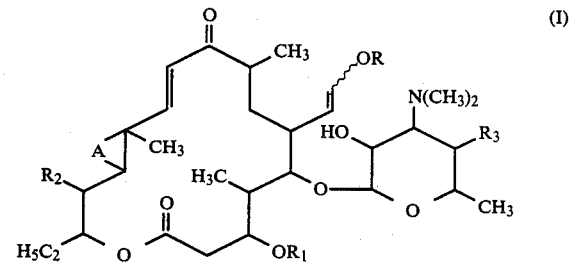

5 Claims, No Drawings

20-O-ACYL-19,20-ENOLMACROLIDE ANTIBIOTIC DERIVATIVES

BACKGROUND OF THE INVENTION

1. Field of the Invention:

This invention relates to novel 16-membered macrolide antibiotic derivatives useful as antibacterial agents, and more specifically to 20-O-acyl-19,20-enolmacrolide antibiotic derivatives and their salts, which can achieve high levels in blood by oral administration.

2. Description of the Prior Art:

As 16-membered macrolide antibiotics, many derivatives, especially, below-described desmycosin derivatives having the general formula (I) in which a formyl group is bonded to the 19-position and O-mycaminosyl-tylonolide (OMT) derivatives have been synthesized and reported to date.

Although they show high antibacterial activities in vitro, they do not show sufficient effects in experiments for the treatment of infected animals by their oral administration. It has been indicated as a possible cause for the above drawback that the 19-formyl group would affect adversely on their absorption characteristics, thereby failing to achieve any high levels in blood. However, there have not been found to date any compounds which have overcome the aforementioned drawback.

SUMMARY OF THE INVENTION

An object of this invention is therefore to provide novel 16-membered macrolide antibiotic derivatives free of the above-mentioned drawbacks.

With the foregoing in view, the present inventors have carried out an extensive investigation to improve their concentration in blood upon oral administration by modifying the 19-formyl group with various groups. As a result, it has now been found that the compounds of the general formula (I), in which the 19-formyl group has been enolacylated, can achieve high levels in blood upon their oral administration and can exhibit excellent antibacterial activities, leading to completion of this invention.

In one aspect of this invention, there is thus provided a 20-O-acyl-19,20-enolmacrolide antibiotic derivative represented by the following general formula (I) or a salt thereof:

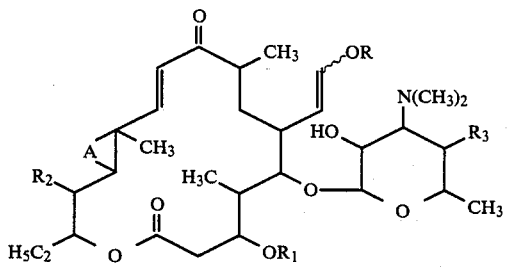

wherein

R: lower alkanoyl or cycloalkyl-lower alkanoyl;
$R_1$: $C_2$–$C_3$ alkanoyl;
$R_2$: H, methyl, —COOR$_4$, —CONHR$_5$, CH$_2$X, —CH$_2$—Q—R$_6$,

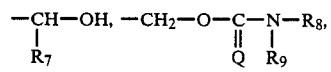

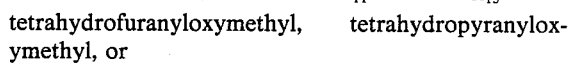

tetrahydrofuranyloxymethyl, tetrahydropyranyloxymethyl, or

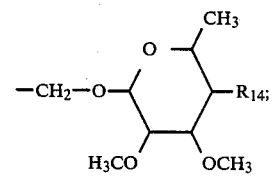

$R_3$: H or hydroxyl;
A: single bond or O;
$R_4$: lower alkyl, aryl, aralkyl, aryl-Q-lower alkyl (Q: will be defined subsequently), $$-\underset{\underset{Y-aryl}{|}}{\overset{}{CH}}-aryl$$

(Y: S or sulfonyl), pyridyl-lower alkyl or thienyl-lower alkyl;
$R_5$: lower alkyl, aryl or aralkyl;
$R_6$: lower alkyl, lower alkanoyl, lower alkylthio-lower alkyl, di(lower alkyl)amino-lower alkyl, aryl or

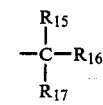

($R_{15}$, $R_{16}$: H, lower alkyl or aryl; $R_{17}$: aryl);
$R_7$: H, lower alkyl, lower alkenyl or aryl;
$R_8$: substituted or unsubstituted lower alkyl;
$R_9$: aryl, aralkyl, thienyl-lower alkyl or substituted or unsubstituted thiazolyl, or $R_8$ and $R_9$ being coupled together with the vicinal nitrogen atom to form a 5–8 membered nitrogen-containing mono- and hetero-cyclic ring;
$R_{10}$: lower alkyl;
$R_{11}$: lower alkyl, cycloalkyl, aryl or aralkyl, or $R_{10}$ and $R_{11}$ being coupled together with the vicinal nitrogen atom to form a 5–8 membered nitrogen-containing mono- and hetero-cyclic ring which may contain another nitrogen atom or oxygen atom;
$R_{12}$: lower alkyl, aryl or aralkyl;
$R_{13}$: H or lower alkyl;
$R_{14}$: H or hydroxyl;
Q: O or S; and
X: halogen atom.

Since the compound of this invention can achieve high level in blood by oral administration, it can be formed into oral antibacterial preparations. It is hence useful.

The above and other objects, features and advantages of the present invention will become apparent from the following description and appended claims.

DETAILED DESCRIPTION OF THE INVENTION AND PREFERRED EMBODIMENTS

The 20-O-acyl-19,20-enolmacrolide antibiotic derivative of this invention may be prepared, for example, by reacting in the presence of a base a carboxylic anhydride represented by ROR (III), in which R has the same meaning as defined above, with a 19-formyl-macrolide antibiotic represented by the following formula (II):

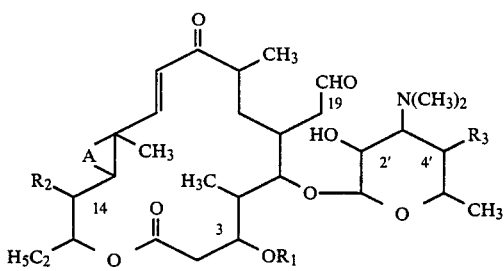

wherein A, $R_1$, $R_2$ and $R_3$ have the same meaning as defined above.

The 19-formyl-macrolide antibiotic (II), one of the starting materials, can be prepared by acylating corresponding one of known compounds represented by the formula (II) in which $R_1$ stands for a hydrogen atom and shown in Table 1.

TABLE 1

| A | $R_2$ | $R_3$ | Publication |
|---|---|---|---|
| O | $CH_3$ | OH | J.A. 22 65 (1969) |
| O | $CH_3$ | H | J.A. 25 641 (1972) |
| single bond | $CH_3$ | H | J.A. 30 450 (1977) |
| single bond | H | H, OH | JPL 120894/1985* |
| single bond | $-COOR_4$ | H, OH | JPL 120893/1985 |
| single bond | $-CONHR_5$ | H, OH | JPL 120896/1985 |
| single bond | $-\underset{\underset{R_7}{\mid}}{CH}-OH$ | H, OH | JPL 215697/1985 |
| single bond | $-CH_2X$ | H, OH | JPL 80398/1982 |
| single bond | $-\underset{\underset{R_{11}}{\mid}}{CH_2N}-R_{10}$ | H, OH | JPL 15997/1983 |
| O, single bond | $-\underset{\underset{R_{13}}{\mid}}{CH_2NCO}-R_{12}$ | H, OH | JPL 33298/1984 |
| single bond | $-\underset{\underset{R_9}{\mid}}{CH_2OCON}-R_8$ | H, OH | JPL 194894/1983 |
| single bond | $-CH_2O-R_6$ | H, OH | JPL 140097/1983 |
| single bond | $-CH_2S-R_6$ | H, OH | JPL 31795/1984 |
| single bond | ![structure with CH2-O, R14, H3CO, OCH3, CH3] | H, OH | JPL 154197/1982 |

*JPL: Japanese Patent Laid-Open No.

In order to obtain a 19-formyl-macrolide antibiotic (II) by reacting a reactive derivative of $R_1$—OH ($R_1$: the same as defined above) with a compound (IV) of the formula (II) in which $R_1$ is a hydrogen atom, the reaction may be conducted by a method known per se in the art. Here, it is preferable to protect, prior to the acylation, the 19-formyl group of the compound (IV) with an acetal forming group and the hydroxyl group in 14-$R_2$ and the 2'- and 4'-hydroxyl groups with protecting groups, which will be described subsequently. Upon removal of the acetal-forming group after the acylation, there is obtained a 19-formylmacrolide antibiotic in which the hydroxyl groups are blocked with the protecting groups. Although these protecting groups may be removed to provide a compound of the formula (II), it is more preferable to conduct the next enolacylation reaction without removal of the protecting groups and then to remove the protecting group after the enolacylation reaction.

As the protecting group or groups for the 2'-hydroxyl group or 2'- and 4'-hydroxyl groups, it is preferable to use those employed routinely in such situations and featuring easy removal after the reaction. Illustrative examples of the protecting groups may include lower alkanoyl groups such as acetyl, propionyl and butyryl, halogenated acetyl groups such as chloroacetyl, dichloroacetyl, trichloroacetyl and trifluoroacetyl, etc. Among these, acetyl groups are particularly preferred.

As a protecting group for a hydroxyl group other than the above-mentioned ones, for example, the 4''-hydroxyl group, it is preferable to use a protecting group which can be removed easily with an acid. For example, tetrahydrofuranyl group, trimethylsilyl group or the like may be mentioned.

The introduction of the above acetyl group is effected by reacting acetic anhydride with the above-mentioned compound (IV) in an inert organic solvent As exemplary inert organic solvents, may be mentioned dichloromethane, chloroform, dichloroethane, acetone, acetonitrile and so on. The reaction temperature may suitably be room temperature or lower.

The enolacylation is effected by reacting a carboxylic anhydride with the compound (II) in the presence of a base such as pyridine or dimethyl aniline. It is preferable to protect each hydroxyl group of the compound (II) prior to the enolacylation. The carboxylic anhydride may preferably be used in an amount 2.5–10 times in moles the compound (II). Although the reaction is brought to completion in 2–150 hours at 50°–120° C., the reaction is allowed to proceed faster even at a lower temperature provided that dimethylaminopyridine (DMAP) is added as a catalyst in a small amount, for example, 0.1–0.5 times in moles the compound (II).

In order to prepare a compound of the formula (I) in which R and $R_1$ are the same alkanoyl groups, the acylation of the 3-hydroxyl group and the enolacylation at the 19-position can be effected simultaneously by reacting a carboxylic anhydride with the compound (IV) in the presence of a base. It is preferable to protect each hydroxyl group of the compound (IV) before the reaction.

Upon removal of the protecting group or groups from the thus-obtained reaction product, the intended compound (I) can be obtained. The removal of the protecting group or groups of the 2'-hydroxyl group or the 2'- and 4'-hydroxyl groups can be effected easily by a method known per se in the art, for example, by treating the reaction product at room temperature in an alcohol or heating same in an alcohol.

The removal of protecting groups for the hydroxyl groups other than those mentioned above can also be conducted by a method known per se in the art, for example, treating the reaction product with an acid in a water-containing hydrophilic organic solvent.

Antibacterial activities of certain compounds (I) of this invention and corresponding 19-formylmacrolide antibiotics as well as their levels in blood and therapeutic effects for infectious diseases upon their oral administration are compared in Table 2.

pressure, thereby obtaining 7.50 g of 2',4'-di-O-acetyl-23-O-dimethylcarbamoyl-OMT dimethylacetal.

The above reaction product (6.88 g) was dissolved in 35 ml of pyridine, followed by addition of 230 mg (0.2 equivalent) of 4-dimethyamino-pyridine and 4.85 ml (4 equivalents) of propionic anhydride). The resultant mixture was stirred at 50° C. for 4 hours. The reaction mixture was then poured into dilute aqueous ammonia, followed by extraction with chloroform. The extract was then concentrated under reduced pressure. The residue was dissolved in 75 ml of acetonitrile which contained 40% of water, followed by an addition of 6 ml of trifluoroacetic acid. The reaction mixture was stirred for 1 hour at room temperature so as to deacetalize the reaction product. The reaction mixture was poured into dilute aqueous ammonia, followed by extraction with chloroform. After drying the extract over anhydrous magnesium sulfate, the extract was evaporated under reduced pressre to obtain 6.75 g of 2',4'-di-O-acetyl-3-O-propionyl-23-O-dimethylcarbamoyl-OMT.

One gram of the above reaction product was dissolved in 5 ml of pyridine, to which 0.634 ml (4 equiva-

TABLE 2

| | | Compound | | | | | |
|---|---|---|---|---|---|---|---|
| | | Ia | Ib | 2a | 2b | 3a | 3b |
| MIC ($\mu$g/ml): S. aureus, 209P | | 0.20 | 0.78 | 0.20 | 0.39 | 0.20 | 0.39 |
| Antibiotics levels in blood upon oral administration at 100 mg/kg to mice (by the paper disk method) | Peak value ($\mu$g/ml) | ND | 3.0 | 0.42 | 2.63 | 0.43 | 2.71 |
| | AUC ($\mu$g · h/ml) | ND | 6.0 | 1.57 | 2.80 | 1.79 | 4.9 |
| Treatment results of infectious diseases of mice by oral administration. Infective microorganism: S. pyogenes, S-23 | MIC ($\mu$g/ml) | 0.10 | 0.78 | — | — | 0.05 | 0.20 |
| | ED$_{50}$ (mg/kg) | >400 | 100–200 | — | — | >200 | 59 |

(Note)
1a: 3-O—Propionyl-23-O—dimethylcarbamoyl-OMT(comparative compound).
1b: 3,20-Di-O—propionyl-19,20-enol-23-O—dimethylcarbamoyl-OMT(invention compound).
2a: 3-O—Propionyl-4''-deoxydesmycosin(comparative compound).
2b: 3,20-Di-O—propionyl-19,20-enol-4''-deoxydesmycosin(invention compound).
3a: 3-O—Propionyl-4'deoxydesmycosin(comparative compound).
3b: 3,20-Di-O—propionyl-19,20-enol-4'deoxydesmycosin(invention compound).
ND: Below detectable limit.

[Examples]

The present invention will hereinafter be described by the following Examples.

EXAMPLE 1

3,20-Di-O-propionyl-19,20-enol-23-O-dimethylcarbamoyl-OMT

Dissolved in 200 ml of dichloroethane was 10.9 g of 2', 4' -di-O-acetyl-23-O-(imidazol-1-yl-carbonyl)-OMT dimethylacetal which had been obtained from 2',4'-di-O-acetyl-OMT dimethylacetal in accordance with the process of Japanese Patent Laid-Open No. 140096/1983. After bubbling dimethylamine through the resultant solution under ice-cooling until saturation, the reaction mixture was stirred for 2 hours at room temperature. After the reaction, the reaction solvent was distilled off under reduced pressure and the residue was charged in a column of silica gel ("Wako Gel C-300", trade name; 300 g), followed by elution with a 7:1 mixed solvent of benzene and acetone. Fractions were collected around Rf=0.45 [carrier: "HPTLC Silica Gel 60F$_{254}$ Art 5642", product of Merck & Co., Inc.; developer: 2:1 mixed solvent of benzene and acetone). The fractions were evaporated to dryness under reduced lents) of propionic anhydride and 75 mg (0.5 equivalent) of 4-dimethylamino-pyridine were added. The reaction mixture was stirred overnight at 55° C. to convert the above reaction product into its corresponding 20-O-acyl-19,20-enolated derivative. After the reaction, the pyridine was distilled off under reduced pressure and the residue was extracted with chloroform. The extract was washed successively with dilute hydrochloric acid and dilute aqueous ammonia, dried through "Whatman 1PS Filter Paper" (trade name), and then concentrated under reduced pressure. The residue was then subjected to column chromatography, namely, the residue was charged in a column of silica gel ("Art 9385", trade name; product of Merck & Co., Inc.; 30 g), and the column was thereafter subjected to gradient elution while changing the benzene/acetone ratio from 20:1 to 12:1, whereby 502 mg of 2',4'-di-O-acetyl- 3,20-di-O-propionyl-19,20-enol-23-O-dimethylcarbamoyl-OMT was obtained.

The above reaction product was dissolved in 5 ml of methanol and the resultant solution was heated at 55° C. for 4–6 hours. The solution was then concentrated under reduced pressure. The residue was subjected to column chromatography, namely, the residue was charged in a column of silica gel ("Art 9385", trade name; product of Merck & Co., Inc.; 15 g), and the column was thereafter subjected to gradient elution while changing the chloroform/methanol ratio from 100:1 to 50:1, thereby obtaining the desired 3,20-di-O-propionyl-19,20-enol-23-O-dimethylcarbamoyl-OMT as a mixture of its cis- and trans-isomers (yield: 295 mg).
PMR (100 MHz, CDCl$_3$) δ ppm: 1.82,1.84 (s,3H), 2.50,2.53 (s,6H), 2.89 (s,6H), 5.83,5.94 (d,H-13), 6.22,6.38 (d,H-10), 7.02,7.14 (d,H-20), 7.24,7.36 (d,H-11).

Mass (CI):
781 (MH$^+$), 763, 707, 651, 460, 248, 230, 192, 174.

High performance liquid chromatography (HPLC) [YMC-GEL'ODS S-5 (Products of Yamamura Chemical Laboratory, Inc), 4×150 mm, 0.2M aqueous solution of NaH$_2$PO$_4$ (pH 2.5) - methanol (4:6), 35° C.]:
12.8 minutes (trans-isomer), 3.5 minutes (cis-isomer).

Cis/trans (determined by NMR coupling constant): 40/47

EXAMPLE 2

20-O-Butyryl-19,20-enol-3-O-propionyl-23-O-dimethylcarbamoyl-OMT

The title compound was obtained by using 0.89 ml of butyric anhydride in lieu of the 0.634 ml of propionic anhydride in the conversion into the 20-O-acyl-19,20-enolated derivative in Example 1.

PMR (100 MHz, CDCl$_3$) δ ppm: 1.84 (br.s,3H), 2.52,2.54 (s,6H), 2.91 (s,6H), 5.86,5.96 (d,H-13), 6.23,6.38 (d,H-10), 7.03,7.15 (d,H-20), 7.26,7.36 (d,H-11).

Mass (CI): 795 (MH$^+$), 721, 651, 530, 460, 262, 244, 192, 74.

HPLC:
19.9 minutes (trans-isomer), 21.0 minutes (cis-isomer).
Cis/trans: 9/51.

EXAMPLE 3

20-O-Isovaleryl-19,20-enol-3-O-propionyl-23-O-dimethylcarbamoyl-OMT

The title compound was obtained by using 0.98 ml of isovaleric anhydride in lieu of the 0.634 ml of propionic anhydride in the conversion into the 20-O-acyl-19,20-enolated derivative in Example 1.

PMR (100 MHz, CDCl$_3$) δ ppm: 1.82,1.84 (s,3H), 2.43 (br.s,2H), 2.51,2.53 (s,6H), 2.90 (s,6H), 5.85,5.95 (d,H-13), 6.21,6.36 (d,H-10), 7.01,7.13 (d,H-20), 7.27,7.36 (d,H-11).

Mass (CI): 809 (MH$^+$), 735, 651, 542, 460, 276, 258, 192, 174.

HPLC: 32.6 minutes (trans-isomer), 35.3 minutes (cis-isomer).
Cis/trans: 31/47.

EXAMPLE 4

Cis-isomer and trans-isomer of 3,20-di-O-propionyl-19,20-enol-23-O-dimethylcarbamoyl-OMT Dissolved in 7 ml of pyridine was 1.5 g of 2′,4′-di-O-acetyl-3-O-propionyl-23-O-dimethylcarbamoyl-OMT which had been obtained in the same manner as in Example 1, followed by addition of propionic anhydride (4 equivalents) and 75 mg of 4-dimethylamino-pyridine. The reaction mixture was stirred overnight at 55° C. After the reaction, the pyridine was distilled off under reduced pressure and the residue was extracted with chloroform. The extract was washed successively with dilute hydrochloric acid and dilute aqueous ammonia, dried through "Whatman 1PS Filter Paper" (trade name), and then concentrated under reduced pressure. The residue was then subjected to column chromatography, namely, the residue was charged in a column of silica gel ("Art 9385", trade name; product of Merck & Co., Inc.; 30 g), and the column was thereafter subjected to gradient elution while changing the benzene/acetone ratio from 20:1 to 12:1. Fractions were collected respectively around Rf=0.58 and Rf=0.61 [carrier: "TLC Silica Gel 60F$_{254}$ Art 5715", product of Merck & Co., Inc.; developer: 3:1 mixed solvent of benzene and acetone]. The fractions were separately evaporated to dryness under reduced pressure, thereby obtaining 478 mg of a fraction rich in the cis-isomer of 2′,4′-di-O-acetyl-3,20-di-O-propionyl-19,20-enol-23-O-dimethylcarbamoyl-OMT and 388 mg of another fraction rich in its trans-isomer. They were again separately subjected to the same column chromatography to obtain 142 mg of the cis-isomer and 213 mg of the trans-isomer of the above reaction product.

The above isomers were separately dissolved in 5 ml portions of methanol. After stirring the resultant solutions separately at 55° C. for 4 hours, they were separately concentrated under reduced pressure. The residues were separately subjected to column chromatography, namely, the residues were separately charged in columns of silica gel ("Art 9385", trade name; product of Merck & Co., Inc.; 15 g), and the columns were thereafter subjected to gradient elution while changing the chloroform/methanol ratio from 100:1 to 50:1, thereby obtaining 96 mg of the cis-isomer and 114 mg of the trans-isomer of 3,20-di-O-propionyl-19,20-enol-23-O-dimethylcarbamoyl-OMT.

Cis-isomer PMR (100 MHz, CDCl$_3$) δ ppm: 1.85 (s,3H), 2.53 (s,6H), 2.89 (s,6H,CON<), 4.14 (m,H-23), 4.25 (d,H-1′), 4.8 (2H,H-15,H-19) 5.36 (m,H-3), 5.83 (d,H-13), 6.37 (d,H-10), 7.14 (d,H-20,J=6.4), 7.25 (d,H-11).

Mass (CI): 781 (MH$^+$), 763, 707, 651, 612, 338, 230, 174. HPLC: 13.9 minutes.

Trans-isomer PMR (100 MHz, CDCl$_3$) δ ppm: 1.82 (s,3H), 2.51 (s,6H), 2.90 (s,6H,CON<), 4.15 (m,H-23), 4.19 (d,H-1′), 4.87 (d.t,H-15) 5.24 (d,H-3), 5.55 (d.d,H-19), 5.95(d,H-13), 6.22 (d,H-10), 7.02 (d,H-20,J=12.5), 7.36 (d,H-11).

Mass (CI): 781 (MH$^+$), 763, 707, 651, 518, 460, 248, 230, 192, 174.

HPLC: 12.7 minutes.

EXAMPLE 5

20-O-Cyclopentylacetyl-19,20-enol-3-O-propionyl-23-O-dimethylcarbamoyl-OMT

Dissolved in 5 ml of pyridine was 1 g of 2′,4′-di-O-acetyl-3-O-propionyl-23-O-dimethylcarbamoyl-OMT which had been obtained in the same manner as in Example 1, followed by addition of 1.24 ml (8 equivalents) of cyclopentylacetic acid, 75 mg of 4-dimethylamino-pyridine and 1.02 g (4 equivalents) of N,N′-dicyclohexyl-carbodiimide (DCC). The reaction mixture was stirred at 55° C. for 70 hours. The precipitated deposit was filtered off and the filtrate was heated under reduced pressure to distil off the pyridine. The residue was extracted with chloroform. The extract was washed successively with dilute hydrochloric acid and dilute aqueous ammonia, dried through "Whatman 1PS Filter Paper" (trade name), and then concentrated under reduced pressure. The residue was then subjected to column chromatography, namely, the residue was charged in a column of silica gel ("Art 9385", trade name; product of Merck & Co., Inc.; 30 g), and the column was thereafter subjected to gradient elution while changing the benzene/acetone ratio from 20:1 to 12:1, whereby 680 mg of 2',4'-di-O-acetyl-20-O-cyclopentylacetyl-19,20-enol-3-O-propionyl-23-dimethylcarbamoyl-OMT was obtained. The reaction product was dissolved in 5 ml of methanol and the resultant solution was heated at 55° C. for 6 hours. The reaction mixture was concentrated under reduced pressure and the residue was subjected to column chromatography, namely, the residue was charged in a column of silica gel ("Art 9385", trade name; product of Merck & Co., Inc.; 15 g), and the column was thereafter subjected to gradient elution while changing the chloroform/methanol ratio from 100:1 to 50:1, thereby obtaining 403 mg of 20-O-cyclopentylacetyl-19,20-enol-3-O-propionyl-23-O-dimethylcarbamoyl-OMT.

PMR (100 MHz, CDCl$_3$) δ ppm: 1.82 (br.s,3H), 2.51,2.54 (s,6H), 2.89 (s,6H), 5.85,5.95 (d,H-13), 6.21,6.36 (d,H-10), 7.01,7.13 (d,H-20), 7.26,7.35 (d,H-11).

Mass (CI): 835 (MH+), 760, 724, 650, 174, 129.
HPLC: 70.3 minutes.

EXAMPLE 6

3,20-Di-O-propionyl-19, 20-enol-4''-deoxydesmycosin

Dissolved in 1.5 ml of dry pyridine was 290 mg of 2',4'-di-O-acetyl-4''-deoxydesmycosin which had been prepared in accordance with the process of Japanese Patent Laid-Open No. 154197/1982, followed by addition of 0.224 ml of propionic anhydride and 43 mg of 4-dimethylamino-pyridine. The resulting mixture was stirred at 60° C. for 20 hours. The reaction mixture was poured into dilute aqueous ammonia, followed by extraction with chloroform. The extract was washed with water, dried through "Whatman 1PS Filter Paper" (trade name), and then concentrated under reduced pressure. The residue was then subjected to column chromatography, namely, the residue was charged in a column of silica gel ("Art 9385", trade name; product of Merck & Co., Inc.), and the column was thereafter subjected to gradient elution while changing the benzene/acetone ratio from 15:1 to 10:1, whereby 108 mg of 2',4'-di-O-acetyl-3,20-di-O-propionyl-19,20-enol-4''-deoxydesmycosin. The reaction product was dissolved in 5 ml of methanol and the resultant solution was heated with stirring at 55° C. for 16 hours. The reaction mixture was then evaporated to dryness under reduced pressure to obtain 96 mg of 3,20-di-O-propionyl-19,20-enol-4''-deoxydesmycosin.

PMR (60 MHz, CDCl$_3$) δ ppm: 1.81 (12-CH$_3$), 2.50 (N(CH$_3$)$_2$), 3.40 (OCH$_3$), 3.45 (OCH$_3$), 4.20 (H-1'), 4.63 (H-1''), 5.22 (H-3), 5.43 (H-19), 5.98 (H-13), 6.20 (H-10), 7.03 (H-20), 7.36 (H-11).

Mass (CI): 868 (MH+), 850, 794, 738, 174, 159.

EXAMPLE 7

3,20-Di-O-propionyl-19,20-enol-4'-deoxydesmycosin

Dissolved in 10 ml of methanol was 2 g of 2'-O-acetyl-4'-deoxydesmycosin which had been prepared in accordance with the process of Japanese Patent Laid-Open No. 154197/1982, followed by an addition of 1 ml of trifluoroacetic acid under ice-cooling. The resulting mixture was stirred for 2 hours at room temperature. Chloroform was added to the reaction mixture, followed by a further addition of dilute aqueous ammonia to conduct extraction. The chloroform layer was washed with water, dried through "Whatman 1PS Filter Paper" (trade name), and then concentrated under reduced pressure, so that 2.21 g of crude 2'-O-acetyl-4'-deoxydesmycosin dimethylacetal was obtained. The reaction product was dissolved in 30 ml of dichloromethane, followed by an addition of 446 μl (2.2 equivalents) of pyridine. While cooling the thus-obtained mixture with a freezing mixture of ice and sodium chloride, 634 ml (2 equivalents) of trimethylsilyl chloride was added. After stirring the mixture as was, 126 μl (0.4 equivalent) of trimethylsilyl chloride was added further. The reaction mixture was then stirred for 6.5 hours. Chloroform and dilute aqueous ammonia were added to the reaction mixture to extract same. The chloroform layer was washed with water, dried through "Whatman 1PS Filter Paper" (trade name), and then concentrated under reduced pressure, so that 2.22 g of crude 2'-O-acetyl-4''-0-trimethylsilyl-4'-deoxydesmycosin dimethylacetal was obtained (yield: 97% based on 2'-O-acetyl-4'-deoxydesmycosin). The reaction product was dissolved in 30 ml of dichloroethane, followed by addition of 633 μl (3 equivalents) of propionyl chloride and 2.79 g (4 equivalents) of tribenzylamine. The resultant mixture was stirred at 70° C. In the course of the stirring, 633 μl of propionyl chloride and 1.40 g (2 equivalents) of tribenzylamine were added further. The stirring was conducted for 7.5 hours. Chloroform and dilute aqueous ammonia were added to the reaction mixture to extract same. The chloroform layer was washed with water, dried through "Whatman 1PS Filter Paper" (trade name), and then concentrated under reduced pressure, thereby obtaining 8.2 g of a residue. The residue was then subjected to column chromatography, namely, the residue was charged in a column of silica gel ("Art 7734", trade name; product of Merck & Co., Inc.; 30g), and the column was thereafter eluted with a 3:1 mixed solvent of benzene and acetone to obtain 1.88 g of 2'-O-acetyl-4''-O-trimethylsilyl-3-O-propionyl-4'-deoxydesmycosin dimethylacetal. The reaction product was added with 38 ml of a 20:16:2 mixed solvent of acetonitrile, water and trifluoroacetic acid and the resulting mixture was stirred for 1 hour at room temperature to conduct both deacetalization and detrimethylsilylation. The reaction mixture was then poured into dilute aqueous ammonia, followed by extraction with chloroform. The extract was washed with water, dried through "Whatman 1PS Filter Paper" (trade name), and then concentrated under reduced pressure, thereby obtaining 1.631 g of crude 2'-O-acetyl-3-O-propionyl-4'-deoxydesmycosin.

In 20 ml of dichloroethane, 1.43 g (1.68 m mol) of the above reaction product was dissolved, followed by addition of 353 μl (3 equivalents) of 2,3-dihydrofuran and 507 mg (1.2 equivalents) of pyridinium p-toluenesulfonate. The resultant mixture was stirred at 55° C. for 7 hours. Chloroform and dilute aqueous ammonia were added to the reaction mixture to extract same. The organic solvent layer was washed with water, dried through "Whatman 1PS Filter Paper" (trade name), and then concentrated under reduced pressure, thereby obtaining 1.75 g of a residue. The residue was then subjected to column chromatography, namely, the residue was charged in a column of silica gel ("Art 7734", trade name; product of Merck & Co., Inc.; 30g), and the column was thereafter eluted first with a 5:1 mixed solvent of benzene and acetone and then with a 3:1 mixed solvent of benzene and acetone to obtain 1.455 g of 2'-O-acetyl-3-O-propionyl-4"-O-tetrahydrofuranyl-4'-deoxydesmycosin.

In 20 ml of pyridine, 1.044 g (1.13 m mol) of the above reaction product was dissolved, followed by an addition of 869 μl (6 equivalents) of propionic anhydride. The resulting mixture was stirred at 90° C. for 143 hours under an argon gas stream. In the course of the stirring, 580 μl (4 equivalents) of propionic anhydride was added further. Saturated saline solution and dilute aqueous ammonia were added to the reaction mixture to extract same with the chloroform. The extract was washed with water, dried through "Whatman 1PS Filter Paper" (trade name), and then concentrated under reduced pressure, thereby obtaining 1.88 g of a residue. The residue was then subjected to column chromatography, namely, the residue was charged in a column of silica gel ("Art 7734", trade name; product of Merck & Co., Inc.; 40g), and the column was thereafter eluted first with a 5:1 mixed solvent of benzene and acetone and then with a 3:1 mixed solvent of benzene and acetone. The thus-obtained active fractions were subjected again to chromatography on a column of 23 g of silica gel to obtain 0.51 g of 3,20-di-O-propionyl-19,20-enol-2'-O-acetyl-4"-O-tetra-hydrofuranyl-4'-deoxydesmycosin. The reaction product was then added with 19 ml of a 10:8:1 mixed solvent of acetonitrile, water and trifluoroacetic acid, followed by stirring for 0.5 hour to effect detetrahydrofuranylation. Dilute aqueous ammonia was added to the reaction mixture, and the resultant mixture was extracted with chloroform. The extract was washed with water, dried through "Whatman 1PS Filter Paper" (trade name), and then concentrated under reduced pressure, thereby obtaining 3,20-di-O-propionyl-19,20-enol-2'-O-acetyl-4'-deoxydesmycosin. It was then dissolved in 20 ml of methanol. After stirring the resulting mixture for 12 hours at room temperature, the reaction mixture was concentrated under reduced pressure to obtain 0.45 g of a crude product. The crude product was charged in a column of silica gel ("Art 7734", trade name; product of Merck & Co., Inc.; 9g), and the column was thereafter eluted with a 50:1 mixed solvent of chloroform and methanol, thereby obtaining 254 mg of 3,20-di-O-propionyl-19,20-enol-4'-deoxydesmycosin in a pure form and 120 mg of an impurity-containing fraction. The impurity-containing fraction was then subjected to column chromatography, namely, the fraction was charged in a column of silica gel ("Art 9385", trade name; product of Merck & Co., Inc.; 4.5g), and the column was thereafter eluted with a 100:1 mixed solvent of chloroform and methanol, thereby additionally obtaining 43 mg of pure 3,20-di-O-propionyl-19,20-enol-4'-deoxydesmycosin. Therefore, 297 mg of 3,20-di-O-propionyl-19,20-enol-4'-deoxydesmycosin was obtained in total.

PMR (Fx-100, CDCl$_3$), δ ppm: 1.8 (s,12-CH$_3$), 2.27 (s,N<), 3.46 (s,2"-OCH$_3$), 3.61 (s,3"-OCH$_3$), 4.14 (d,H-1'), 4.56 (d,H-1"), 4.8 (m, H-15), 5.9 (d,H-13), 6.25 (d,H-10), 6.98 (d,H-20), 7.38 (d,H-11).

MS (CI): MH+ (did not appear), 850 (MH+-18), 794, 231, 214, 200, 174, 158.

EXAMPLE 8

3,20,4"-Tri-O-propionyl-19,20-enol-4'-deoxydesmycosin

Dissolved in 6 ml of pyridine was 1.2 g (1.51 m mol) of 2'-O-acetyl-4'-deoxydesmycosin, followed by addition of 92 mg (0.5 equivalent) of 4-dimethylaminopyridine and 1.16 ml (6 equivalents) of propionic anhydride. The resulting mixture was stirred at 55° C. for 17 hours. The reaction mixture was poured into a mixture of saturated saline solution and dilute aqueous ammonia, followed by extraction with chloroform. The extract was washed with water, dried through "Whatman 1PS Filter Paper" (trade name), and then concentrated under reduced pressure. The residue was then subjected to column chromatography, namely, the residue was charged in a column of silica gel ("Art 7734", trade name; product of Merck & Co., Inc.; 20 g), and the column was thereafter eluted with a 4:1 mixed solvent of benzene and acetone, thereby obtaining 705 mg of 3,20,4"-tri-O-propionyl-19,20-enol-2'-O-acetyl-4'-deoxydesmycosin. The reaction product was then dissolved in 10 ml of methanol and the resultant mixture was stirred for 15 hours at room temperature. The reaction mixture was concentrated under reduced pressure, and the resulting residue was subjected to column chromatography, namely, the residue was charged in a column of silica gel ("Art 7734", trade name; product of Merck & Co., Inc.; 20 g), and the column was thereafter eluted with a 100:1 mixed solvent of chloroform and methanol, thereby obtaining 351 mg of 3,20,4"-tri-O-propionyl-19,20-enol-4'-deoxydesmycosin (yield: 25%).

PMR (Fx-100, CDCl$_3$), δ ppm: 1.79 (s,12-CH$_3$), 2.34 (s,N<), 3.45 (s,2"-OCH$_3$), 3.51 (s,3"-OCH$_3$), 4.15 (d,H-1'), 4.4 (d.d,H-4"), 4.61 (d,H-1"), 5.2 (br.d, H-3), 5.6 (br.d,H-19), 5.9 (br.d,H-13), 6.24 (d,H-10,trans), 6.4 (d,H-10,cis), 7.04 (d,H-20,trans,J=12Hz), 7.36 (d,H-11).

MS (CI):
924 (MH+), 850, 794, 231, 174, 158.

EXAMPLE 9

3,20,4"-Tri-O-isobutyryl-19.,20-enol-4'-deoxydesmycosin

Dissolved in 20 ml of dichloromethane was 1049 mg (1.39 m mol) of 4'-deoxydesmycosin, followed by an addition of 393 μl (3 equivalents) of acetic anhydride. The resulting mixture was stirred for 2.5 hours at room temperature. The reaction mixture was added with 7% aqueous ammonia and was then extracted with chloroform. The extract was washed with saturated saline solution, dried through "Whatman 1PS Filter Paper" (trade name), and then concentrated under reduced pressure, thereby obtaining 1.14 g of 2'-O-acetyl- 4'-deoxydesmycosin.

In 16 ml of pyridine, 800 mg (1 m mol) of the above reaction product was dissolved, followed by an addition of 2.49 ml (15 equivalents) of isobutyric anhydride. The resultant mixture was stirred at 90° C. for 92 hours under an argon gas stream. The reaction mixture was then poured into ammonia-containing saturated saline solution, followed by extraction with chloroform. The extract was washed with saturated saline solution, dried through "Whatman 1PS Filter Paper" (trade name), and then concentrated under reduced pressure, thereby obtaining 2.5 g of an oily substance. The oily substance was then subjected to column chromatography, namely, the oily substance was charged in a column of silica gel ("Art 7734", trade name; product of Merck & Co., Inc.; 25 g), and the column was thereafter eluted with a 7:1 mixed solvent of benzene and acetone, thereby obtaining 0.30 g of 3,20,4"-tri-O-isobutyryl-19,20-enol-2'-O-acetyl-4'deoxydesmycosin. The thus-obtained reaction product was thereafter dissolved in 20 ml of methanol. After stirring the resultant mixture for 13 hours at room temperature, the mixture was concentrated under reduced pressure to obtain 274 mg of a crude product. The crude product was then subjected to column chromatography, namely, the crude product was charged in a column of silica gel ("Art 7734", trade name; product of Merck & Co., Inc.; 10 g), and the column was thereafter eluted with a 3:1 mixed solvent of benzene and acetone, thereby obtaining 184 mg of 3,20,4''-tri-O-isobutyryl-19,20-enol-4'-deoxydesmycosin (yield: 19%).

PMR (Fx-100, CDCl$_3$), δ ppm: 2.28 (s,N<), 2.31 (s,N<), 3.45 (s,2''-OCH$_3$), 3.51 (s,3''-OCH$_3$).

MS (CI): 966 (MH$^+$) 878.

EXAMPLE 10

3,4''-Di-O-propionyl-20-O-isobutyryl-19,20-enol-4'-deoxydesmycosin

Dissolved in 4 ml of pyridine was 0.66 g (0.736 m mol) of 2'-O-acetyl-4'-deoxydesmycosin, followed by addition of 45 mg (0.5 equivalent) of 4-dimethyl-aminopyridine and 566 µl (6 equivalents) of propionic anhydride. The resulting mixture was stirred at 55° C. for 1 hour. The reaction mixture was poured into ammonia-containing saline solution, followed by extraction with chloroform. The extract was washed with saturated saline solution, dried through "Whatman 1PS Filter Paper" (trade name), and then concentrated under reduced pressure, thereby obtaining 0.79 g of 3,4''-O-propionyl-2'-O-acetyl-4'-deoxydesmycosin in a crude form. It was then dissolved in 10 ml of pyridine, followed by an addition of 1.3 ml (10 equivalents) of isobutyric anhydride. The resulting mixture was stirred at 90° C. for 64 hours under an argon gas stream. The reaction mixture was poured into ammonia-containing saturated saline solution, followed by extraction with chloroform. The extract was washed with saline solution, dried through "Whatman 1PS Filter Paper" (trade name), and then concentrated under reduced pressure. The residue was then subjected to column chromatography, namely, the residue was charged in a column of silica gel ("Art 7734", trade name; product of Merck & Co., Inc.; 14 g), and the column was thereafter subjected to gradient elution while changing the benzene/acetone ratio from 10:1 to 7:1, thereby obtaining 0.39 g of 3,4''-di-O-propionyl-20-O-isobutyryl-19,20-enol-2'-O-acetyl-4'-deoxydesmycosin. The above reaction product was then dissolved in 10 ml of methanol and the resultant mixture was stirred for 20 hours at room temperature. The reaction mixture was concentrated to dryness under reduced pressure to obtain 0.34 g of 3,4''-di-O-propionyl-20-O-isobutyryl-19,20-enol-4'-deoxydesmycosin (yield: 49%).

PMR (Fx-100, CDCl$_3$), δ ppm: 2.27 (s,N<), 2.29 (s,N<), 3.45 (s,2''-OCH$_3$), 3.51 (s,3''-OCH$_3$)

MS (CI): 938 (MH+), 864.

EXAMPLE 11

3,20-Di-O-acetyl-19,20-enol-23,4'-di-deoxy-23-dimethylamino-OMT

Dissolved in 8 ml of dichloromethane was 400 mg of 23,4'-di-deoxy-23-dimethylamino-OMT which had been prepared in accordance with the process of Japanese Patent Laid-Open No. 15997/1983, followed by an addition of 248 µl (4 equivalents) of acetic anhydride. The resulting mixture was stirred for 3 hours at room temperature. The reaction mixture was added with 7% aqueous ammonia, followed by extraction with chloroform. The extract was washed with saline solution, dried through "Whatman 1PS Filter Paper" (trade name), and then concentrated under reduced pressure, thereby obtaining 380 mg of 2'-O-acetyl-23,4'-di-deoxy-23-dimethylamino-OMT in a crude form.

In 5 ml of pyridine, 319 mg (0.49 m mol) of the above reaction product was dissolved, followed by an addition of 464 ml (10 equivalents) of acetic anhydride. The resultant mixture was stirred at 90° C. for 63 hours. Dilute aqueous ammonia was added to the reaction mixture, followed by extraction with chloroform. The extract was washed with saline solution, dried through "Whatman 1PS Filter Paper" (trade name), and then concentrated under reduced pressure. The residue was then subjected to column chromatography, namely, the residue was charged in a column of silica gel ("Art 7734", trade name; product of Merck & Co., Inc., 8 g), and the column was thereafter eluted with a 30:1 mixed solvent of chloroform and methanol to obtain 272 mg of 3,20,2'-tri-O-acetyl-19,20-enol-23,4'-di-deoxy-23-dimethyl-amino-OMT. The reaction product was dissolved in 10 ml of methanol and the resultant solution was stirred for 41 hours at room temperature. The reaction mixture was then concentrated under reduced pressure to obtain 185 mg of a residue. The residue was then subjected to column chromatography, namely, the residue was charged in a column of silica gel ("Art 7734", trade name; product of Merck & Co., Inc., 10 g), and the column was thereafter eluted with a 30:1 mixed solvent of chloroform and methanol to obtain 106 mg of 3,20-di-O-acetyl-19,20-enol-23,4'-di-deoxy-23-dimethylamino-OMT. PMR (Fx-100, CDC;$_3$) δ ppm: 1.82 (s,12-CH3), 2.04,2.07 (each, s,3,20-COCH$_3$), 2.18 (s,23-N<), 2.28 (s,3'-N<), 4.15,4.20 (each, d,H-1',J=6.9Hz), 4.64 (m,H-15), 5.15 (br.d,H-3,J=12Hz), 5.70,5.80 (each, br.d,H-13,J=10Hz), 6.27,6.41 (each, d,H-10,J=16Hz), 6.97 (d,H-20,J=12.5Hz,trans), 7.05 (d,H-20,J=6.4Hz,cis), 7.29,7.40 (each, d,H-ll,J=16Hz).

MS (CI): 693 (MH+), 651, 633, 158.

Having now fully described the invention, it will be apparent to one of ordinary skill in the art that many changes and modifications can be made thereto without departing from the spirit or scope of the invention as set forth herein.

We claim:

1. A compound represented by the following formula:

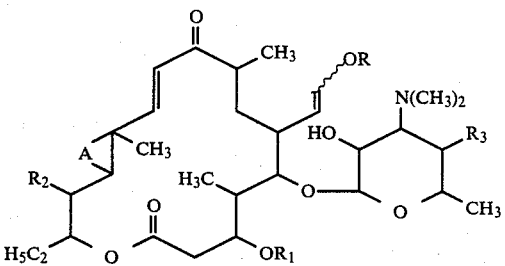

wherein
R: lower alkanyoyl or cycloalkyl-lower alkanoyl;
R$_1$: C$_2$-C$_4$ alkanoyl;
R$_2$: H, methyl, —COOR$_4$, —CONHR$_5$, CH$_2$X, —CH$_2$—Q—R$_6$,

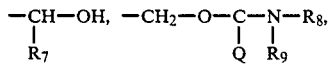

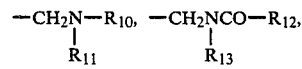

tetrahydrofuranyloxymethyl, tetrahydropyranyloxymethyl, or

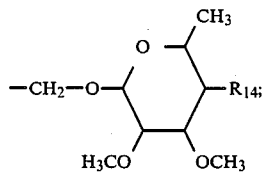

$R_3$: H or hydroxyl;
A: single bond or O;
$R_4$: lower alkyl;
$R_5$: lower alkyl, phenyl or benzyl;
$R_6$: lower alkyl, lower alkanoyl, lower alkylthio-lower alkyl, di(lower alkyl)amino-lower alkyl, phenyl or

($R_{15}$, $R_{16}$: H, lower alkyl or phenyl; $R_{17}$: phenyl);
$R_7$: H, lower alkyl, lower alkenyl or phenyl;
$R_8$: lower alkyl which may be substituted by lower alkoxycarbonyl group;
$R_9$: lower alkyl, phenyl, benzyl, thienyl-lower alkyl or 2-amino-4-thiazolyl group in which the amino group may be protected, or $R_8$ and $R_9$ being coupled together with the vicinal nitrogen atom to form a 5-8 membered nitrogen-containing mono- and hetero-cyclic ring;
$R_{10}$: lower alkyl;
$R_{11}$: lower alkyl, cycloalkyl or benzyl, or $R_{10}$ and $R_{11}$ being coupled together with the vicinal nitrogen atom to form a 5-8 membered nitrogen-containing mono- and hetero-cyclic ring which may contain another nitrogen atom or oxygen atom;
$R_{12}$: lower alkyl, phenyl or benzyl,
$R_{13}$: H or lower alkyl;
$R_{14}$: H, hydroxyl or lower alkyl;
Q: O or S; and
X: halogen atom, or a salt thereof.

2. The compound or salt thereof as claimed in claim 1, wherein in the formula, A means a single bond, and $R_2$ denotes

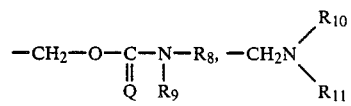

($R_8$, $R_9$, $R_{10}$, $R_{11}$ and Q having the same meaning as defined in claim 1) or

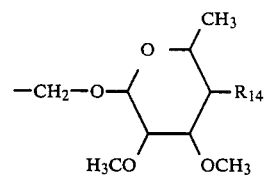

($R_{14}$ having the same meaining as defined in claim 1).

3. The compound or salt thereof as claimed in claim 1, wherein in the formula, A means a single bond, and $R_2$ denotes

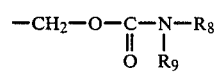

($R_8$ and $R_9$ means lower alkyl).

4. The compound or salt thereof as claimed in claim 1, wherein in the formula, A means a single bond, and $R_2$ denotes

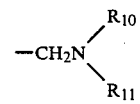

($R_{10}$ and $R_{11}$ means lower alkyl).

5. The compound or salt thereof as claimed in claim 1, wherein in the formula, A means a single bond, and $R_2$ denotes

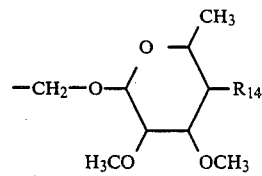

($R_{14}$ means H, hydroxyl or lower alkyl).

* * * * *

UNITED STATES PATENT AND TRADEMARK OFFICE
CERTIFICATE OF CORRECTION

PATENT NO. : 4,804,749

DATED : Feb. 14, 1989

INVENTOR(S) : Tatsuro FUJIWARA, et al.

It is certified that error appears in the above-identified patent and that said Letters Patent is hereby corrected as shown below:

On the title page
The name of the first inventor is corrected as follows:

-- Tatsuro FUJIWARA --

Signed and Sealed this

Tenth Day of October, 1989

Attest:

DONALD J. QUIGG

Attesting Officer

Commissioner of Patents and Trademarks